(12) United States Patent
Diolaiti et al.

(10) Patent No.: US 11,344,376 B2
(45) Date of Patent: May 31, 2022

(54) SYSTEMS AND METHODS FOR FLEXIBLE COMPUTER-ASSISTED INSTRUMENT CONTROL

(71) Applicant: INTUITIVE SURGICAL OPERATIONS, INC., Sunnyvale, CA (US)

(72) Inventors: Nicola Diolaiti, Menlo Park, CA (US); Samuel Y. Chang, Mountain View, CA (US); Vincent Duindam, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 418 days.

(21) Appl. No.: 16/311,514

(22) PCT Filed: Jun. 30, 2017

(86) PCT No.: PCT/US2017/040214
§ 371 (c)(1),
(2) Date: Dec. 19, 2018

(87) PCT Pub. No.: WO2018/005928
PCT Pub. Date: Jan. 4, 2018

(65) Prior Publication Data
US 2019/0231449 A1     Aug. 1, 2019

Related U.S. Application Data

(60) Provisional application No. 62/357,555, filed on Jul. 1, 2016.

(51) Int. Cl.
*A61B 34/30*     (2016.01)
*A61B 1/005*     (2006.01)
(Continued)

(52) U.S. Cl.
CPC .......... *A61B 34/30* (2016.02); *A61B 1/00006* (2013.01); *A61B 1/0016* (2013.01);
(Continued)

(58) Field of Classification Search
CPC ..... A61B 34/30; A61B 34/37; A61B 1/00006; A61B 1/0016; A61B 1/00078;
(Continued)

(56) References Cited

U.S. PATENT DOCUMENTS 6,380,732 B1    4/2002   Gilboa et al.
6,389,187 B1    5/2002   Greenaway et al.
(Continued)

FOREIGN PATENT DOCUMENTS

CN    203763034 U    8/2014
JP    H06292652 A    10/1994
(Continued)

OTHER PUBLICATIONS

International Preliminary Report on Patentability for Application No. PCT/US2017/040214, dated Jan. 10, 2019, 12 pages.
(Continued)

*Primary Examiner* — Kathleen S Holwerda
*Assistant Examiner* — Uyen N Vo
(74) *Attorney, Agent, or Firm* — Haynes and Boone, LLP

(57) ABSTRACT

A computer-assisted medical system comprises a flexible elongate instrument. The flexible elongate instrument comprises a plurality of wires extending from a proximal end of the flexible elongate instrument to a distal end of the flexible elongate instrument. Each wire of the plurality of wires may be used to steer the distal end. The system also comprises a control system coupled to the flexible elongate instrument. The control system is configured to monitor movement of the flexible elongate instrument along a longitudinal central axis and determine an extent of motion of the flexible
(Continued)

elongate instrument in a first direction along the longitudinal central axis based on the monitoring. The control system is also configured to alter a rigidity of the flexible elongate instrument based on a rigidity profile relative to the extent of motion by adjusting one or more forces applied by the plurality of wires to the distal end of the flexible elongate instrument.

20 Claims, 9 Drawing Sheets

(51) Int. Cl.
| | | |
|---|---|---|
| *A61B 34/35* | (2016.01) | |
| *A61B 34/37* | (2016.01) | |
| *G02B 23/24* | (2006.01) | |
| *A61B 1/00* | (2006.01) | |
| *A61B 34/00* | (2016.01) | |
| *A61M 25/01* | (2006.01) | |
| *A61B 34/20* | (2016.01) | |
| *A61B 17/00* | (2006.01) | |

(52) U.S. Cl.
CPC ........ *A61B 1/0057* (2013.01); *A61B 1/00078* (2013.01); *A61B 34/35* (2016.02); *A61B 34/37* (2016.02); *A61B 34/71* (2016.02); *A61B 34/74* (2016.02); *A61M 25/0147* (2013.01); *G02B 23/2476* (2013.01); *A61B 2017/00336* (2013.01); *A61B 2034/2061* (2016.02); *A61B 2034/301* (2016.02); *A61B 2034/742* (2016.02)

(58) Field of Classification Search
CPC ......... A61B 34/74; A61B 34/71; A61B 34/35; A61B 1/0057; A61B 2034/742; A61B 2034/2061; A61B 2017/00336; A61B 2034/301; A61B 2034/306; A61B 2034/2055; A61B 2034/2059; A61B 2034/2051; A61B 34/20; A61B 2090/061; G02B 23/2476; A61M 25/0147
See application file for complete search history.

(56) References Cited

U.S. PATENT DOCUMENTS

| | | | |
|---|---|---|---|
| 7,316,681 | B2 | 1/2008 | Madhani et al. |
| 7,772,541 | B2 | 8/2010 | Froggatt et al. |
| 8,900,131 | B2 | 12/2014 | Chopra et al. |
| 9,259,274 | B2 | 2/2016 | Prisco et al. |
| 9,452,276 | B2 | 9/2016 | Duindam et al. |
| 2006/0013523 | A1 | 1/2006 | Childlers et al. |
| 2006/0089531 | A1* | 4/2006 | Tartaglia ............ A61B 1/00154 600/114 |
| 2007/0135683 | A1 | 6/2007 | Bob et al. |
| 2007/0239170 | A1* | 10/2007 | Brock ...................... B25J 9/104 606/108 |
| 2010/0016757 | A1 | 1/2010 | Greenburg et al. |
| 2012/0289777 | A1* | 11/2012 | Chopra ................ A61B 1/2676 600/109 |
| 2013/0096497 | A1 | 4/2013 | Duindam et al. |
| 2015/0011830 | A1* | 1/2015 | Hunter ................. A61B 1/0052 600/118 |
| 2015/0148690 | A1 | 5/2015 | Chopra et al. |
| 2018/0303319 | A1 | 10/2018 | Ikeda et al. |

FOREIGN PATENT DOCUMENTS

| | | |
|---|---|---|
| WO | WO-2015153174 A1 | 10/2015 |
| WO | WO-2016025465 A1 | 2/2016 |
| WO | WO-2016040079 A1 | 1/2017 |
| WO | WO-2017109986 A1 | 6/2017 |

OTHER PUBLICATIONS

International Search Report and Written Opinion for Application No. PCT/US2017/040214, dated Sep. 8, 2017, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP17821332.8 dated Dec. 16, 2019, 8 pages.

\* cited by examiner

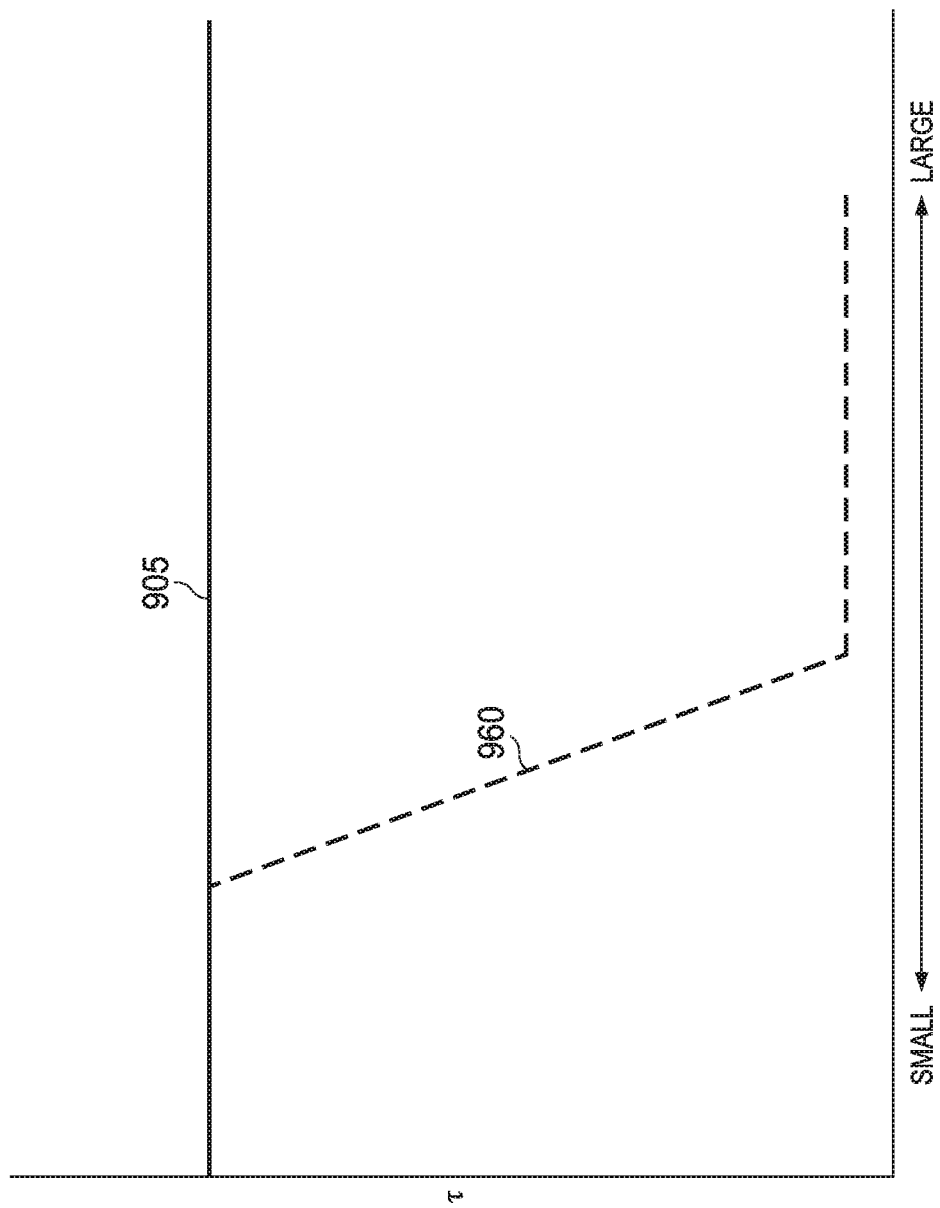

SYSTEMS AND METHODS FOR FLEXIBLE COMPUTER-ASSISTED INSTRUMENT CONTROL

RELATED APPLICATIONS

This patent application is the U.S. national phase of International Application No. PCT/US2017/040214, filed Jun. 30, 2017, which designated the U.S. and claims priority to and the benefit of the filing date of U.S. Provisional Patent Application 62/357,555, entitled "SYSTEMS AND METHODS FOR FLEXIBLE COMPUTER-ASSISTED INSTRUMENT CONTROL," filed Jul. 1, 2016, which are incorporated by reference in their entirety.

FIELD

The present disclosure is directed to systems and methods for computer-assisted medical procedures, and more particularly to systems and methods for controlling a flexible elongate instrument.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physicians may insert minimally invasive medical instruments (including surgical, diagnostic, therapeutic, or biopsy instruments) to reach a tissue location. To assist with reaching the target location, the location and movement of the medical instruments may be correlated with pre-operative or intra-operative images of the patient anatomy. With the image-guided instruments correlated to the images, the instruments may navigate natural or surgically created passageways in anatomic systems such as the intestines, the kidneys, the brain, the heart, the circulatory system, lungs, urethras, arteries, umbilical lines, and/or the like. Medical tools are needed that are flexible enough to safely navigate the tight beds of the anatomic passageways while providing sufficient rigidity to ensure a predictable performance direction when deployed from a delivery catheter toward the target tissue.

SUMMARY

The embodiments of the invention are best summarized by the claims that follow the description. Consistent with some embodiments, a computer-assisted medical system comprises a flexible elongate instrument. The flexible elongate instrument comprises a plurality of wires extending from a proximal end of the flexible elongate instrument to a distal end of the flexible elongate instrument. Each wire of the plurality of wires may be used to steer the distal end. The system also comprises a control system coupled to the flexible elongate instrument. The control system is configured to monitor movement of the flexible elongate instrument along a longitudinal central axis and determine an extent of motion of the flexible elongate instrument in a first direction along the longitudinal central axis based on the monitoring. The control system is also configured to alter a rigidity of the flexible elongate instrument based on a rigidity profile relative to the extent of motion by adjusting one or more forces applied by the plurality of wires to the distal end of the flexible elongate instrument.

Consistent with some embodiments, a method of controlling a medical device, comprises monitoring commanded movement of a flexible elongate instrument. The flexible elongate instrument comprises a plurality of wires extending from a proximal end of the flexible elongate instrument to a distal end of the flexible elongate instrument. Each of the plurality of wires may be used to steer the distal end of the flexible elongate instrument. The commanded movement is provided through an input device. The method also comprises determining an extent of a commanded motion of the flexible elongate instrument based on the monitoring and altering a rigidity of the flexible elongate instrument based on a rigidity profile relative to the extent of the motion by adjusting one or more forces applied by each of the plurality of wires to the distal end of the flexible elongate instrument.

Consistent with some embodiments, a non-transitory machine-readable medium comprises a plurality of machine-readable instructions which, when executed by one or more processors associated with a flexible elongate instrument, are adapted to cause the one or more processors to perform a method. The method comprises monitoring movement of the flexible elongate instrument. The flexible elongate instrument comprises a plurality of wires extending from a proximal end of the flexible elongate instrument to a distal end of the flexible elongate instrument. Each of the plurality of wires may be used to steer the distal end of the flexible elongate instrument. The method also comprises determining an extent of a motion of the flexible elongate instrument based on the monitoring and altering a rigidity of the flexible elongate instrument based on a rigidity profile relative to the extent of the motion by adjusting one or more forces applied by each of the plurality of wires to the distal end of the flexible elongate instrument.

Consistent with some embodiments, a computer-assisted medical system comprises a flexible elongate instrument comprising a plurality of wires extending from a proximal end of the flexible elongate instrument to a distal end of the flexible elongate instrument. Each wire of the plurality of wires may be used to steer the distal end. The system also comprises a control system coupled to the flexible elongate instrument. The control system is configured to monitor movement of the flexible elongate instrument and determine a mode of operation for the flexible elongate instrument. The mode of operation corresponds to one of a retraction mode, an insertion mode, and a parking mode. In response to a determination that the mode of operation is the retraction mode, the control system is configured to determine an extent of a retraction of the flexible elongate instrument based on the monitoring and reduce a rigidity of the flexible elongate instrument based on the extent of the retraction by adjusting one or more forces applied by the plurality of wires to the distal end of the flexible elongate instrument. In response to a determination that the mode of operation is the insertion mode, the control system is configured to determine an extent of a insertion of the flexible elongate instrument based on the monitoring. The control system is also configured to increase the rigidity of the flexible elongate instrument based on the extent of the insertion by adjusting the one or more forces applied by the plurality of wires to the distal end of the flexible elongate instrument. In response to a determination that the mode of operation is the parking mode, the control system is configured to determine an extent of a parking of the flexible elongate instrument based on the monitoring and increase or decrease the rigidity of the flexible elongate instrument based on the extent of the parking by adjusting the one or more forces applied by the plurality of wires to the distal end of the flexible elongate instrument.

BRIEF DESCRIPTIONS OF THE DRAWINGS

FIGS. 9-10 illustrates sub-mode rigidity profiles.

Figure 1:
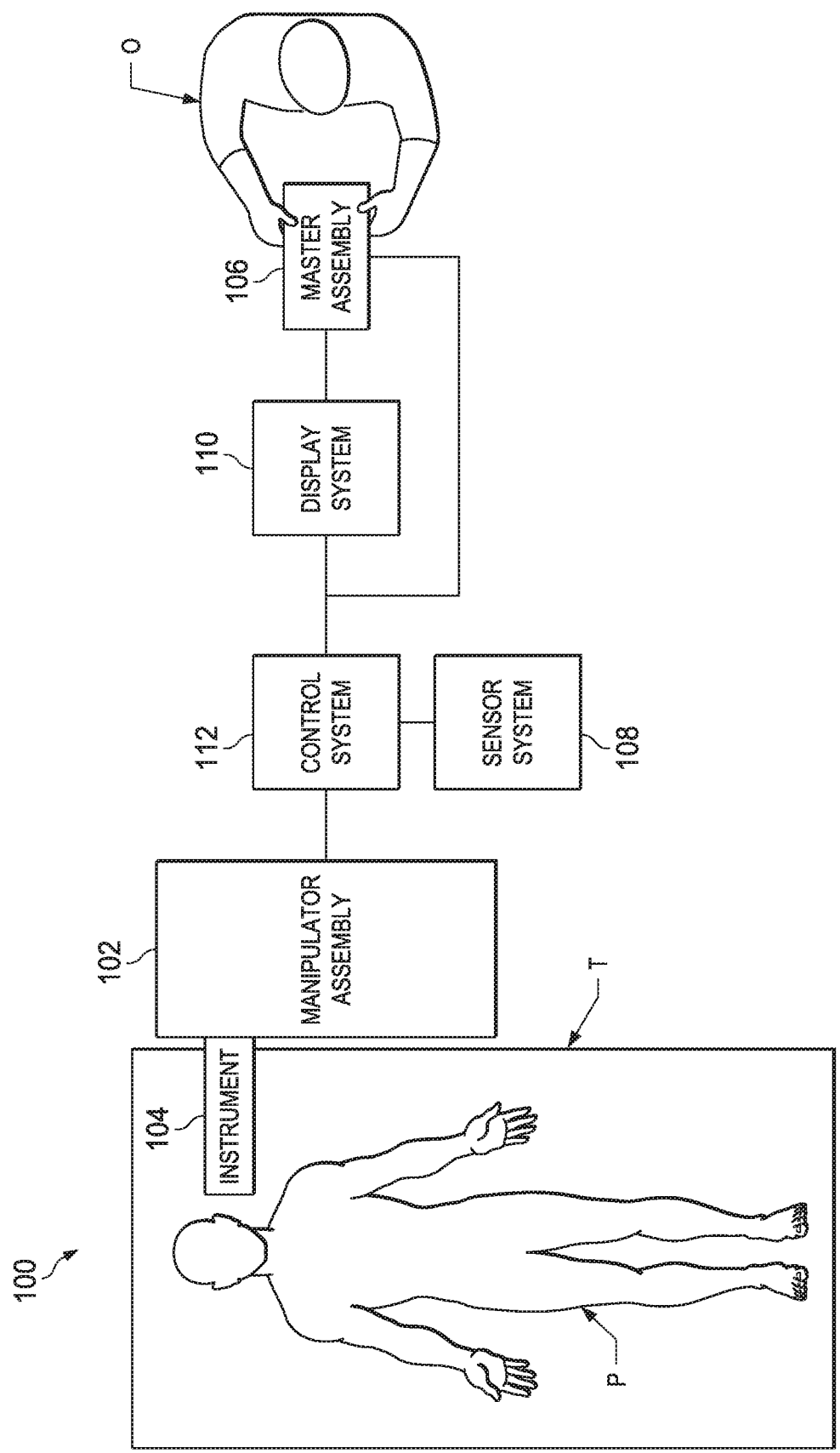
FIG. 1 is an exemplary teleoperated medical system.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object. Components described as "coupled" may be electrically or mechanically directly coupled, or they may be indirectly coupled via one or more intermediate components.

Long, flexible devices, such as catheters, have a small cross section that include one or more hollow openings along their length and are desirable for inserting medical instruments and/or devices into narrow passageways of a patient, such as airways in lungs and/or the like. Steering the leading or distal end of a catheter through passageways makes it easier to control which passageways the catheter enters.

One possible way of steering the leading end of these catheters is by actuators pushing and/or pulling a series of wires that run along the long, flexible device. Using these wires, an operator and/or an automated system is able to pull and/or push harder on one side of the leading end relative to another so as bend the leading end in a desired direction relative to the rest of the device.

In addition to steering the leading end, pushing and/or pulling the wires harder also affects how rigid or stiff the leading end becomes. This is not generally a problem when the bend in the leading end aligns with the passageway in which the leading end is inserted, but this may not be the case when the leading end is further inserted into and/or retracted from the passageways without aligning it with the current passageway. For example, the leading end could be bent over into a "hook" shape to insert the leading end around a curve in the passageways, but when the leading end is later retracted, this "hook" may prevent the leading end from being negotiated through a straighter and/or differently curved region of the passageways. One way of accounting for the possibility of hooking is to reverse the steering used to insert the leading end when the leading end is later retracted. Another approach is to reduce the rigidity of the leading end so that as it is retracted, it can more easily adjust its shape based on the current passageway. The rigidity of the leading end may be adjusted by changing the amount of force applied by the wires used to steer the leading end. For example, to reduce the rigidity, the amount of force applied to the wires is reduced accordingly. The amount of force applied by the wires may be controlled using motors and/or actuators that can push and/or pull on the wires. Consequently, the rigidity can be adjusted by altering a force and/or a torque applied by the motors/actuators to control the pushing and/or pulling of one or more of the wires in the catheter. A controlled reduction in the rigidity may reduce the likelihood of disorientation of an operator controlling movement of the catheter. Adjustment of rigidity may proceed according to a predefined plan or profile of how quickly the rigidity is adjusted. A rigidity profile may have different zones of behavior for the rigidity of the catheter; for example, the rigidity may be decreased faster in one zone than in other zones.

During the insertion mode, it may be desirable to increase the rigidity so that the catheter can be steered as it is moving forward inside the patient passageway. The rigidity may be increased to a maximum allowable rigidity for the catheter.

When the catheter is not moving much, the rigidity can be adjusted to higher or lower levels. Rigidity may be increased when the catheter is not moving much in order to provide stability to an instrument being deployed through the catheter while a procedure is being performed.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator (e.g., a surgeon, a clinician, or a physician O as illustrated in FIG. 1) to view the interventional site and to control teleoperational manipulator assembly 102.

Master assembly 106 may be located at a surgeon's console which is usually located in the same room as operating table T, such as at the side of a surgical table on which patient P is located. However, it should be understood that physician O can be located in a different room or a completely different building from patient P. Master assembly 106 generally includes one or more control devices for controlling teleoperational manipulator assembly 102. The control devices may include any number of a variety of input devices, such as joysticks, trackballs, scroll wheels, data gloves, trigger-guns, hand-operated controllers, voice recognition devices, body motion or presence sensors, and/or the like which may be operated by the physician O to provide a commanded motion. To provide physician O a strong sense of directly controlling instruments 104 the control devices may be provided with the same degrees of freedom as the associated medical instrument 104. In this manner, the control devices provide physician O with telepresence or the perception that the control devices are integral with medical instruments 104.

In some embodiments, the control devices may have more or fewer degrees of freedom than the associated medical instrument 104 and still provide physician O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so physician O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or physician O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. In some examples, the endoscope may include one or more mechanisms for cleaning one or more lenses of the endoscope when the one or more lenses become partially and/or fully obscured by fluids and/or other materials encountered by the endoscope. In some examples, the one or more cleaning mechanisms may optionally include an air and/or other gas delivery system that is usable to emit a puff of air and/or other gasses to blow the one or more lenses clean. Examples of the one or more cleaning mechanisms are discussed in more detail in international Publication No. WO/2016/025465 (filed Aug. 11, 2016) (disclosing "Systems and Methods for Cleaning an Endoscopic Instrument"), which is incorporated by reference herein in its entirety. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of physician O. In this manner physician O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the physician O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist physician O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the physician O with a virtual image of medical instrument 104 within the surgical site from an external viewpoint. An image of a portion of medical instrument 104 or other graphical or alphanumeric indicators may be superimposed on the virtual image to assist physician O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to physician O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 2:
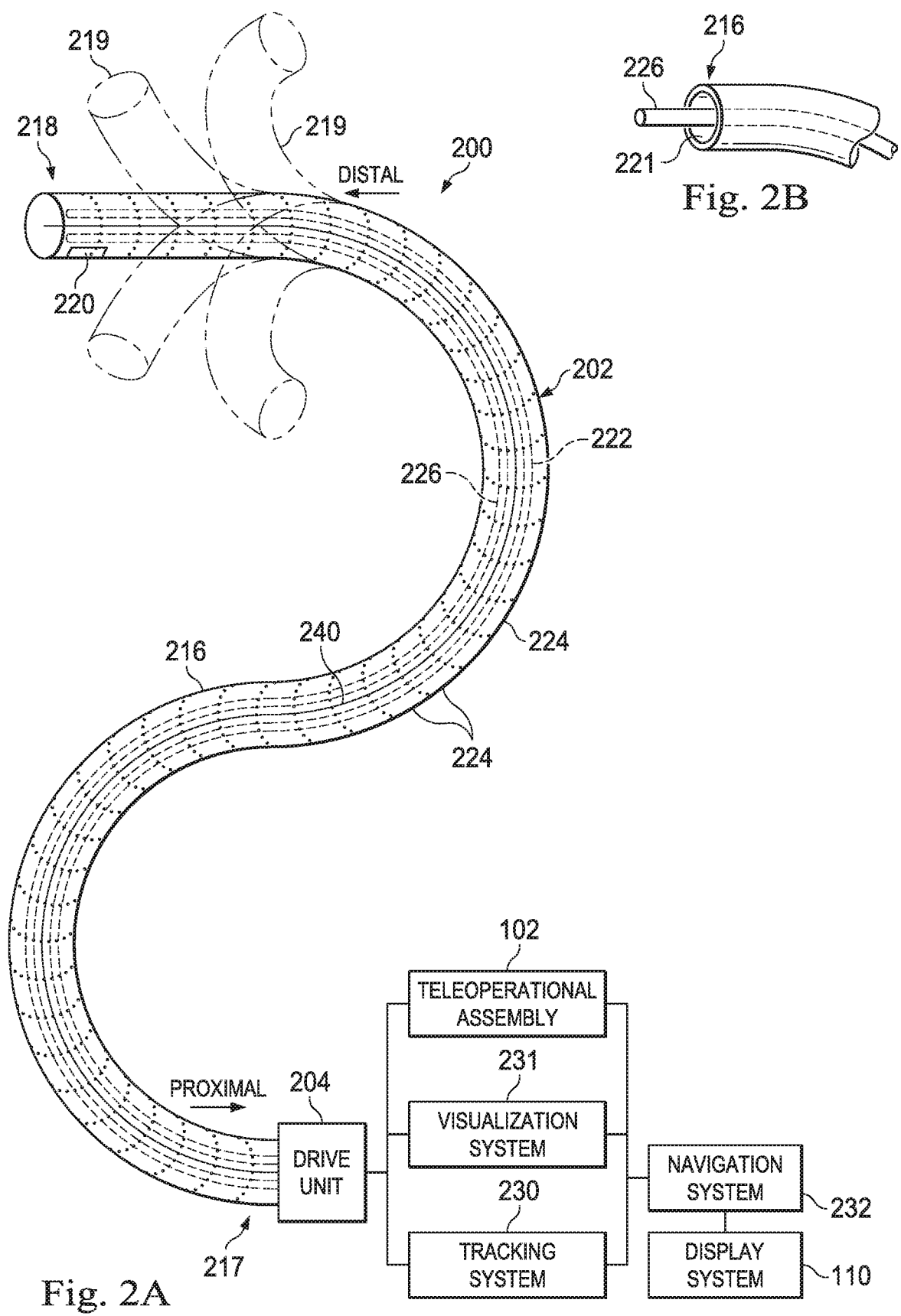
FIG. 2A is an exemplary medical instrument system.
FIG. 2B is an exemplary distal end of a flexible elongate instrument.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end 218 (or tip portion 218). In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may use any appropriate sensing technology or combination of sensing technologies, such as: OFDR (optical frequency domain reflectometry) techniques such as those using Fiber Bragg gratings, Raleigh scattering, or some other applicable reflection approach; position sensors enabled by EM (electromagnetic) techniques; linear rotary encoder techniques supported by capacitive, optical, resistive, or other technologies; etc. As a specific example, position sensor system 220 may comprise, or be a component of, an electromagnetic (EM) sensor system including one or more conductive coils that may be subjected to an externally generated electromagnetic field. Each coil of such an EM sensor system used to implement position sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of position sensors (not shown), such as electromagnetic (EM) sensors similar to the sensors used in some embodiments of position sensor system 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like.

Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. Pat. No. 9,259,274 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. In some examples, the actuator(s) can be used to actuate an articulable end effector of medical instrument 226, such as for grasping tissue in the jaws of a biopsy device or the like. One or more actuator position sensors such as resolvers, encoders, potentiometers, and/or other mechanisms may provide sensor data to the teleoperational assembly including position and/or rotation information for the actuators and/or the one or more wires 240. In some examples, this sensor data may be used to determine motion of distal end 218 and/or one or more end effectors being manipulated by actuators. In some examples, this sensor data may be used to calculate forces and/or torques being applied by wires 240. Actuators are discussed in more detail below.

Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

In some embodiments, control system 112 is configured to apply commands to teleoperational manipulator assembly 102 and/or to one or more actuators, which control bending of distal end 218 of flexible body 216 through the use of steer controls, which may include one or more gears, levers, pulleys, cables, wires, rods, bands, and/or the like and/or any combination of these approaches. The steering controls are then used to transmit actions from the one or more inputs along the shaft of the surgical instrument and to actuate distal end 218. In some examples, the commands include one or more instructions stored in a memory. These instructions may be executed by a processor (e.g., a processor of the control system 112).

According to some embodiments, flexible body 216 may be steered within some passageway of patient P. As flexible body 216 makes contact with walls of the passageway, there may be external forces which push against flexible body 216 from the passageway, and vice versa. In some examples, the external forces may be determined using one or more force and/or pressure sensors located on or inside flexible body 216. Depending upon the magnitude of force applied to the pushing and/or pulling on wires 240, a rigidity or stiffness of flexible body 216 may optionally be controlled so that the ability of flexible body to resist and/or reduce the external forces, which may cause flexible body to bend, may optionally be adjusted. In some examples, the higher the magnitude of the force applied to the wires 240, the higher the rigidity exhibited by flexible body 216.

Figure 3:
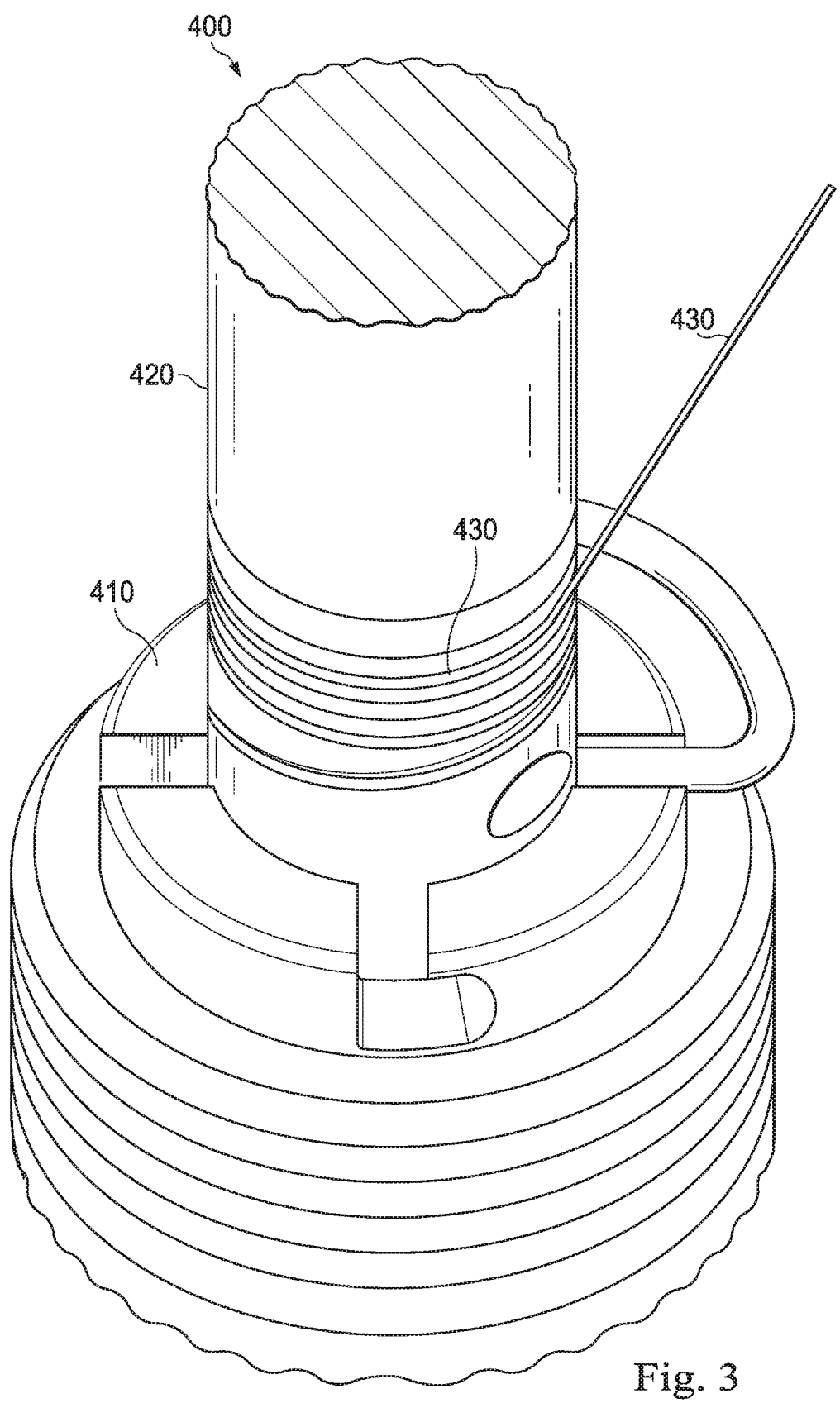
FIG. 3 is an exemplary actuator.

FIG. 3 illustrates an exemplary actuator 400, such as an actuator contained within drive unit 204. In some examples, actuator 400, as shown in FIG. 3, is based on a rotational actuation approach in which a rotating spindle 410 is rotated to actuate a controllable degree of freedom (DOF). Rotating spindle 410 is coupled to a drive shaft 420 which may be the drive shaft of a motor, servo, active actuator, hydraulic actuator, pneumatic actuator, and/or the like and/or any combination of these approaches (not shown). As torque is applied to drive shaft 420 and rotating spindle 410 is rotated, a wire 430 attached to rotating spindle 410 and/or drive shaft 420 may be further wrapped around and/or unwrapped from around rotating spindle 410 and/or drive shaft 420.

According to some embodiments, wire 430 may correspond to any of wires 240-242 and/or wires 310-340. In some examples, rotation of rotating spindle 410 and drive shaft 420 and the corresponding wrapping and/or unwrapping of wire 430 may result in a pushing force and/or pulling force on wire 430. In some examples, monitoring a rotation angle and/or rotational velocity of rotating spindle 410 and/or drive shaft 420 may also provide an indication of how far wire 430 is being released and/or pulled. Thus, when actuator 400 is used in conjunction with the wires 240, the rotation angle and/or rotational velocity of rotating spindle 410 and/or drive shaft 420 and/or the torque applied by actuator 400 to drive shaft 420 may provide useful feedback on the forces applied to wire 430 and thus the steering to be applied at the distal end (e.g., distal end 218) of medical instrument system 200 by wire 430. Which way distal end 218 will bend may depend upon the placement of wire 430 with respect to other wires that are also contributing to steering.

In some embodiments, releasing or reducing the force in the wires of the catheter body may cause a corresponding reduced stiffness or rigidity in the catheter. Similarly, applying or increasing a pulling or pushing force in the wires of the catheter body may cause an increase in stiffness or rigidity of the catheter. This stiffness may be the physical stiffness or rigidity of the catheter body material. For example, the material of the catheter body may become stiffer with multiple steering wires pulled concurrently. Alternatively, the stiffness or rigidity of the catheter may be a closed-loop stiffness or rigidity controlled by the control system. The closed-loop catheter control system and methods are described, for example, in U.S. patent application Ser. No. 13/274,198 (filed Oct. 14, 2011) (disclosing "Catheters with Control Modes for Interchangeable Probes") which is incorporated by reference herein in its entirety.

In some examples, drive shaft 420 may provide force and/or torque feedback information to medical instrument 104 and control system 112. In some examples, position sensors such as resolvers, encoders, potentiometers, and other mechanisms may provide data to the teleoperational assembly regarding the rotation and/or orientation of drive shaft 420 and/or rotating spindle 410. In some examples, actuator 400 may be used in conjunction with the wires 240 to respond to external forces acting on distal end 218 and measured by one or more force and/or pressure sensors. In some examples, an external force detected by the one or more force and/or pressure sensors may optionally be compensated for by actuating a corresponding wire, to steer distal end 218 toward or away from the external force.

Figure 4A:
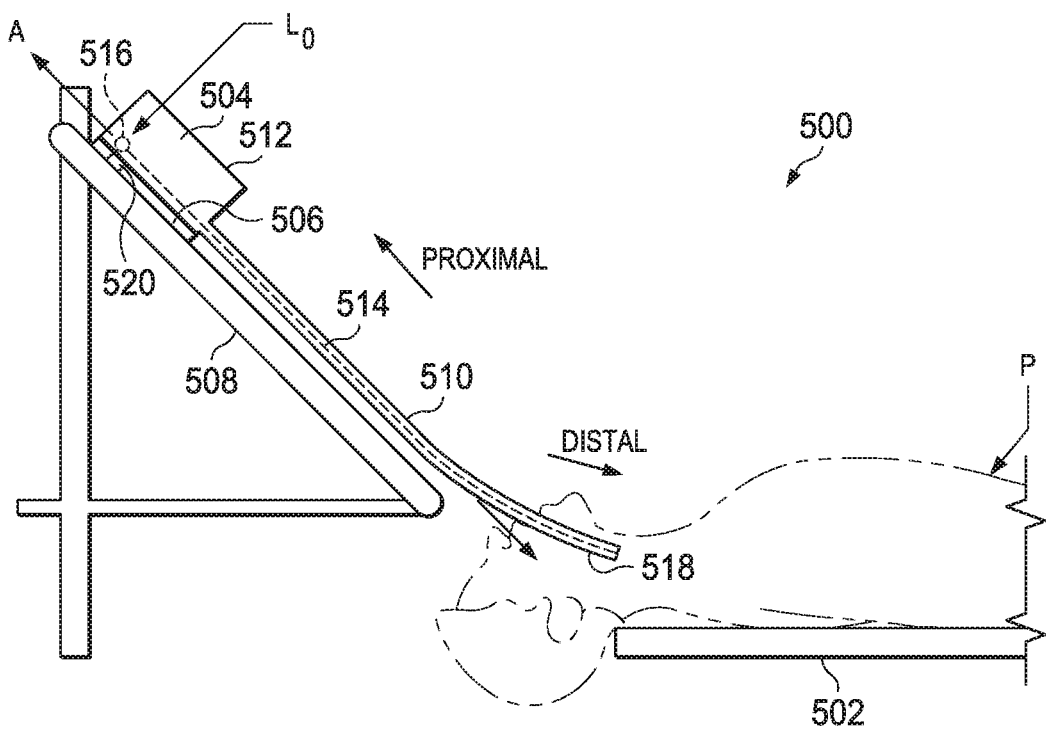
FIGS. 4A and 4B illustrate side views of a patient coordinate space including a medical instrument mounted on an insertion assembly.
Figure 4B:
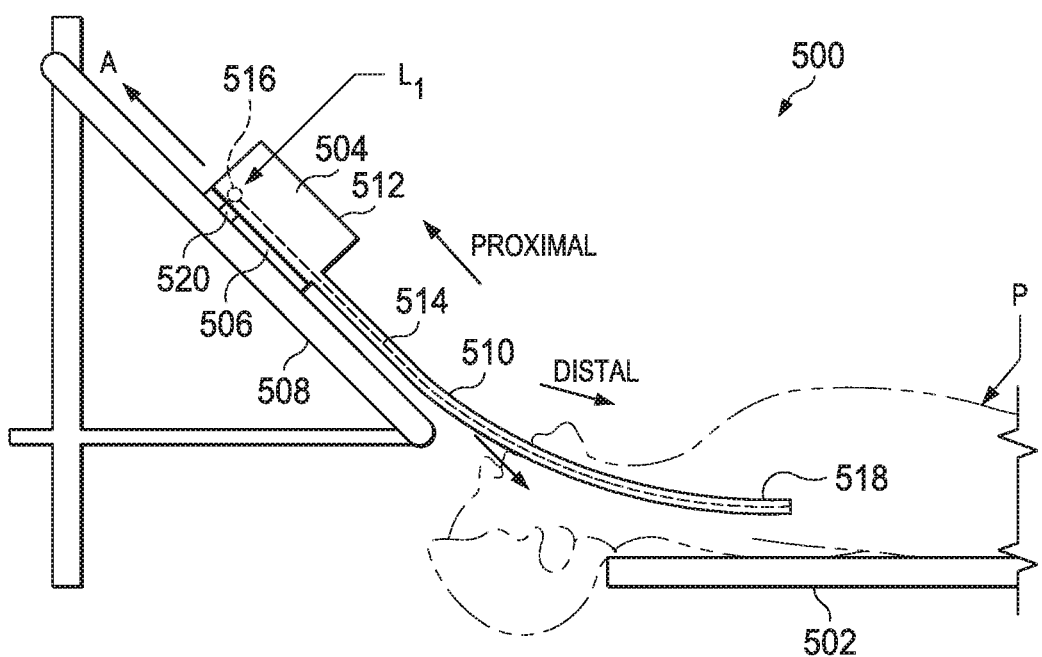

FIGS. 4A and 4B are simplified diagrams of side views of a patient coordinate space including a medical instrument mounted on an insertion assembly, according to some embodiments. As shown in FIGS. 4A and 4B, a surgical environment 500 includes a patient positioned on platform 502. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific phase in respiration and tagged and identified with that phase. In some embodiments, the phase during which data is collected may be inferred from physiological information collected from patient P. Within surgical environment 500, a point gathering instrument 504 is coupled to an instrument carriage 506. In some embodiments, point gathering instrument 504 may use EM sensors, shape-sensors, and/or other sensor modalities. As the measurement points are collected from within the passageways of patient P, the points are stored in a data storage device, such as a memory. The set of measured points may be stored in a database that includes at least some, but may include all, of the measured points obtained during the procedure or immediately before the procedure. As stored in memory, each of the points may be represented by data comprising coordinates of the point, a timestamp, and/or a relative sensor position or individual sensor ID (when multiple sensors distributed along a length of the point gathering instrument 504 are used to determine the location of several points simultaneously).

Instrument carriage 506 is mounted to an insertion stage 508 fixed within surgical environment 500. Alternatively, insertion stage 508 may be movable but may also have a known location (e.g., via a tracking sensor or other tracking device) within surgical environment 500. Instrument carriage 506 may be a component of a teleoperational manipulator assembly (e.g., teleoperational manipulator assembly 102) that couples to point gathering instrument 504 to control insertion motion (i.e., motion along the A axis) and, optionally, motion of distal end 518 of a flexible elongate instrument 510 in multiple directions including yaw, pitch, and roll. In some examples, flexible elongate instrument 510 corresponds with instrument system 200 and/or flexible body 300. Instrument carriage 506 or insertion stage 508 may include actuators, such as servomotors, (not shown) that control motion of instrument carriage 506 along insertion stage 508.

Elongate instrument 510 is coupled to an instrument body 512. Instrument body 512 is coupled and fixed relative to instrument carriage 506. In some examples, an optical fiber shape sensor 514 is fixed at a proximal point 516 on instrument body 512. In some embodiments, proximal point 516 of optical fiber shape sensor 514 may be movable along instrument body 512 and the location of proximal point 516 may be known (e.g., via a tracking sensor or other tracking device). Shape sensor 514 measures a shape from proximal point 516 to another point such as distal end 518 of elongate instrument 510. In some examples, point gathering instrument 504 may be similar to medical instrument system 200.

A position measuring device 520 provides information about the position of the instrument body 512 as it moves on insertion stage 508 along a retraction and/or insertion axis A (such as a direction along the longitudinal central axis of the instrument body). The position measuring device 520 may include resolvers, encoders, potentiometers, and other sensors that determine the rotation and orientation of drive shafts controlling the motion of the instrument carriage 506 and consequently the motion of the instrument body 512. In some embodiments, insertion stage 508 is linear. In some examples, insertion stage 508 may be curved or have a combination of curved and linear sections.

FIG. 4A shows instrument body 512 and instrument carriage 506 in a retracted position along insertion stage 508. In this retracted position, proximal point 516 is at a position $L_0$ on axis A. In this position along insertion stage 508 an A component of the location of proximal point 516 may be set to a zero and/or another reference value to provide a base reference to describe the position of instrument carriage 506, and thus proximal point 516, on insertion stage 508. With this retracted position of instrument body 512 and instrument carriage 506, distal end 518 of elongate instrument 510 may be positioned just inside an entry orifice of patient P. Also in this position, position measuring device may be set to a zero and/or another reference value (e.g., I=0). In FIG. 4B, instrument body 512 and instrument carriage 506 have advanced along the linear track of insertion stage 508 and distal end 518 of flexible elongate instrument 510 has advanced into patient P. In this advanced position, the proximal point 516 is at a position $L_1$ on the A-axis. In some examples, encoder and/or other position data from one or more actuators controlling movement of instrument carriage 506 along insertion stage 508 and/or one or more position sensors associated with instrument carriage 506 and/or insertion stage 508 is used to determine the position $L_A$ of proximal point 516 relative to position $L_0$. In some examples, position $L_1$ may further be used as an indicator of the distance or the insertion depth to which distal end 518 of elongate instrument 510 is inserted into the passageways of the anatomy of patient P. In alternative examples, the flexible elongate instrument 510 can be advanced to a position causing the proximal point 516 to be at a position beyond $L_1$.

Flexible elongate instrument 510 may be advanced from position $L_0$, advanced or retracted from any position between $L_0$ and the advanced position $L_1$, or advanced or retracted from any position beyond $L_1$. During the retraction, it may be desirable that distal end 518 have a decreased rigidity so as to reduce the risk of harm to patient P and/or damage to flexible elongate instrument 510. Rigidity in the flexible instrument during retraction could cause a force to be applied by distal end 518 against the walls of the passageways, resulting in abrasion. To prevent damage to the anatomic passageways, the rigidity of distal end 518 may be decreased during the retraction such that any contact with the walls of the passageway and resulting force from the contact may be reduced. In some procedures, retraction occurs in the context of making minor position adjustments or small, quick reciprocal motion. In such procedures, an abrupt full slackening of the flexible instrument during retraction may be undesirable because full slackening could change the orientation (i.e., the pointing direction) of the distal end of the instrument. Therefore, in some embodiments, adjusting the rigidity of the flexible instrument gradually based on an elapsed time or distance traveled during a movement mode may be more suitable. This may allow for minor retraction motion and subsequent insertion motion without alteration of the orientation of the distal end of the instrument. In such embodiments, it may be advantageous to control the increase or decrease in the rigidity of flexible elongate instrument according to a rigidity profile as described in FIGS. 5A and 5B. Alternatively, the rigidity adjustment may have a stepwise profile with no rigidity adjustment for a period of time until a threshold time, distance, or speed is achieved, followed by full slackening after the threshold is reached.

In some embodiments, flexible elongate instrument 510 may be parked within passageways of the anatomy of patient P such that it is not being inserted or retracted. While parked, it may be desirable to increase the rigidity, or place the elongate instrument in a "locked" mode in order to provide stability to an instrument deployed through flexible elongate instrument 510 as a procedure is performed. Alternatively, it may be desirable to keep the rigidity relatively constant, decrease the rigidity so that any contact with the walls of the passageway and resulting force from this contact may be reduced or, as with the retraction or insertion, it would be advantageous to control the rigidity of flexible elongate instrument 510 according to a rigidity profile.

Figure 5A:
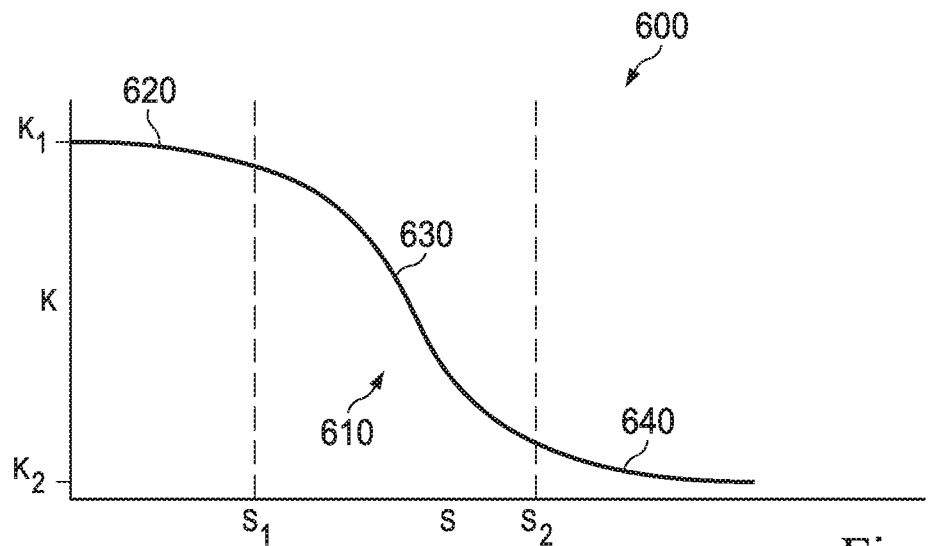
FIGS. 5A and 5B are exemplary rigidity profiles for a flexible elongate instrument.
Figure 5B:
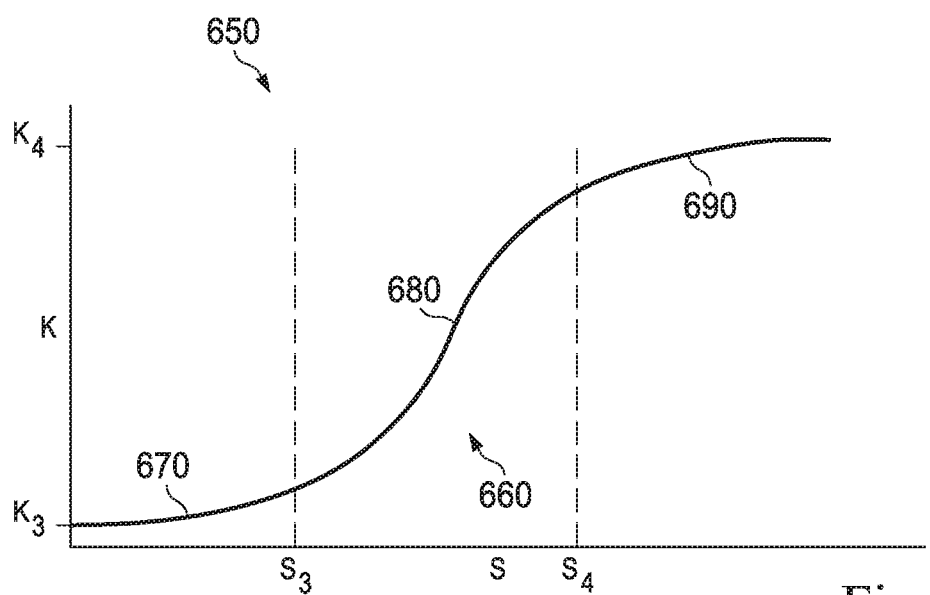

FIGS. 5A and 5B are exemplary rigidity profiles 600 and 650, respectively, for a flexible elongate instrument, such as flexible body 216 and/or flexible elongate instrument 510. Rigidity profiles 600 and 650 are graphical representations of possible variations of the rigidity or stiffness, illustrated by curves 610 and 660, respectively. Curves 610 and 660 show how the rigidity, designated by k, may be adjusted as a function of a parameter designated by S representing an extent of a movement mode such as insertion, retraction, or park. In some examples, control system 112 is configured to apply one or more of rigidity profiles 600 and/or 650 to the flexible elongate instrument during a procedure.

According to some embodiments, S may represent a distance or a change in distance, for example a change in the insertion depth or a retraction distance for the flexible elongate instrument or the distance traveled as a percentage of a largest insertion depth value by the flexible elongate instrument through patient passageways. According to other embodiments, S may represent other variables that may be used to characterize an extent of the retraction, insertion, and/or parking for the flexible elongate instrument. For example, S may represent an elapsed insertion time, elapsed retraction time, elapsed parking time, change in insertion depth, retraction distance, velocity, speed, and/or the like and/or any combination thereof. Alternatively, S may represent an elapsed time since the insertion, retraction, or parking began.

Rigidity value k may range between an initial value (e.g., $k_1$, $k_3$) and a final value (e.g., $k_2$, $k_4$) over the course of an instrument movement mode such as retraction, insertion or parking. In some examples, the lowest rigidity value (e.g. $k_2$, $k_3$) may correspond to a desired nominal value, such as zero or a small but non-zero rigidity. The desired nominal rigidity value may be operator-selected, based on the size of one or more actuators actuating the flexible elongate instrument, based on the ability of the flexible elongate instrument to bend in response to anatomic motions, based on a procedure being performed, and/or the like and/or any combination of these approaches.

As shown in FIGS. 5A and 5B, the rigidity profiles 600 and 650 can be organized in different zones of behavior for the rigidity of the flexible elongate instrument as exemplified by curves 610 and 660. For example, FIG. 5A includes zones 620, 630, 640 and FIG. 5B includes zones 670, 680, 690. Each zone may represent an elapsed S period such as a different distance traveled or a different period of time, and the curves 610 and 660 can represent different rates of change of rigidity value k in different zones. Some zones such as zones 620, 640, 670, 690 may serve as transition zones where the rigidity value k is kept relatively constant as S increases, so that the rigidity profile may smoothly transition at the beginning and ending of a movement mode such as retraction, insertion or parking. In other zones, such as zones 630, 680, the rate of change in rigidity value k is greater. In these examples, the zones of greatest rigidity rate change occur near the middle of a movement mode, but in other examples, the zone of greatest rigidity rate change may occur at other periods of the movement mode. In some examples, rigidity profiles 600 and/or 650 may optionally include additional zones (not shown) with corresponding functions of rigidity. In some examples, a rigidity profile may feature a combination of rigidity profiles 600 and 650. In some embodiments, rigidity profiles 600 and/or 650 may optionally include any combination of linear, non-linear, exponential, logarithmic, step, piece-wise, hyperbolic, parabolic, periodic/trigonometric, inverse hyperbolic, polynomial, modular, other monotonic functions, and/or the like and/or any combination thereof. In some examples, rigidity profiles may also include a hysteresis or memory feature in which the adjustment in stiffness in one direction S (for example when moving from small to large values) is different than in the opposite direction of S. In general, rigidity adjustment profiles may depend in a linear or nonlinear way on variables other than S, such as the derivative of S, the integral of S, or any combination thereof, or on other additional variables.

Rigidity profile 600 and/or 650 may be used to adjust forces applied by one or more actuators to one or more wires, such as any of wires 240, 430 used to control the steering of the distal end of the flexible elongate instrument. For example, rigidity profile 600 and/or 650 may be used to adjust a force and/or a torque applied by the one or more actuators to control the pushing and/or pulling of one or more of the one or more wires within the flexible elongate instrument. When adjusting a force and/or torque applied by one or more actuators, rigidity profile 600 and/or 650 may implement a scaling factor and/or torque multiplier used to scale a force and/or torque that is applied by the one or more actuators. In some examples, the scaling factor or torque multiplier may range from 1.0 or near 1.0 for $k_1$ to a nominal, possibly non-zero value for $k_2$. In some examples, the scaling factor or torque multiplier may range from a nominal, possibly non-zero value for $k_3$ to 1.0 or near 1.0 for $k_4$. In some examples, rigidity profiles 600 and/or 650 may represent a function that is dependent upon additional factors such as an external force applied to the flexible elongate instrument, a shape of the flexible elongate instrument, a sensitivity of the anatomy forming the passageways, a curvature of the anatomy, one or more operator preferences, and/or the like and/or any combination of these approaches. In some examples, the rigidity may correspond to an aggregation of the individual forces on each wire, e.g., by average, weighted sum, and/or the like and/or any combination of these approaches.

Referring to FIG. 5A, an example of a rigidity profile is shown during the retraction mode of an elongate flexible device. By applying rigidity profile 600 during the retraction mode, the rigidity of the flexible elongate instrument is decreased, and consequently any contact force from the flexible elongate instrument applied to the anatomic tissue, such as a wall of a passageway, may be reduced. In addition, the controlled reduction in the rigidity may be particularly suitable when the instrument is being adjusted, being moved in a reciprocal motion, or otherwise being retracted relatively small distances before becoming parked or transitioning to an insertion movement.

Generally, an instrument with an applied rigidity profile 600 would experience only a slight decrease in rigidity in zone 620, a greater decrease in rigidity in zone 630, and a relatively steady relaxes state in zone 640. More specifically, in a first zone 620, the rigidity is approximately maintained at an initial rigidity, $k_1$, or decreases slightly below $k_1$ as S is increased and the retraction begins to occur. In a second zone 630, starting at $S_1$, the rigidity is decreased at a faster rate than at first zone 620 as S further increases and additional retraction occurs with the likelihood of contact between a distal end of the flexible elongate instrument and walls of the passageways increasing. Rigidity may be decreased at a faster rate, causing the instrument to more quickly lose stiffness and therefore reduce the possible damage to the patient that a rigid instrument would cause. In a third zone 640, starting at $S_2$, the rigidity is tapered to a near constant desired final value, $k_2$, as the retraction distance continues to increase.

Referring to FIG. 5B, an example of a rigidity profile is shown during the insertion mode of an elongate flexible device. In this example, S can represent a distance traveled or time period during insertion mode. In the example of FIG. 5B, rigidity profile 650 is a minor image of rigidity profile 600, and may optionally be used to increase the rigidity during the insertion and/or parking of the flexible elongate instrument in order to allow control of the distal end as the flexible elongate instrument advances and/or is held steady within a passageway. Generally, an instrument with an applied rigidity profile 650 would experience only a slight increase in rigidity in zone 670, a greater increase in rigidity in zone 680, and a relatively steady rigid state in zone 690. More specifically, in a first zone 670, the rigidity is approximately maintained at an initial rigidity, $k_3$, or increases slightly above $k_3$ as S is increased when the insertion and/or parking begins. In a second zone 680, the rigidity is increased at a faster rate than at first zone 670 as S further increases. In FIG. 5B, the rigidity is increased at a faster rate at second zone 680 as S further increases. In a third zone 690, the rigidity is tapered to a near constant desired final value, $k_4$, as S continues to increase. In some examples, $k_4$ may correspond to a desired maximum rigidity. The desired maximum rigidity may be operator-selected, based on the size of one or more actuators actuating the flexible elongate instrument, based on a procedure being performed, a safety ceiling, and/or the like and/or any combination of these approaches.

In some embodiments, a rigidity profile similar to rigidity profile 600 or rigidity profile 650 may be applied when the flexible instrument enters a parking mode. For example, if the flexible instrument enters the parking mode from a retraction mode, the flexible instrument may be stiffened while in the parking mode. With some rigidity profiles applied during the parking mode, the rigidity may increase or decrease more quickly because the flexible instrument is not moving.

In some embodiments, first zone 620/670 and/or third zone 640/690 are optional. Rigidity profile 600/650 may have different shapes and/or regions than those depicted in curve 610/660. As shown, rigidity profile 600/650 is a smooth function, such that it is at least continuously differentiable within its zone, or rigidity profile 600/650 may be one continuous function through zones 620/670-640/690. Alternatively, rigidity profile 600/650 is not continuously differentiable at starting and/or ending points between one or more of zones 620/670-640/690. In some examples, rigidity profile 600/650 is a constant at first zone 620/670 at an initial value $k_1$. At second zone 63/6800, starting at $S_1$, the rigidity may decrease linearly as S is increased until third zone 640/690 at $S_2$. Rigidity profile 600/650 may optionally include a series of steps, starting at an initial value $k_1$ at first zone 620/670, and stepping down or up to a desired final value $k_2$ at second zone 630/680. In some examples, shape of curve 610/660 is representative of a logistic function. In some examples, rigidity profile 600/650 is a monotonic decreasing or increasing function to ensure that there is a decrease, increase and/or no change in the rigidity throughout the motion of the flexible elongate instrument.

Although the systems and methods of this disclosure have been described for use in the connected airways of the lung, they are also suited for navigation and treatment of other tissues, via natural or surgically created connected passageways, in any of a variety of anatomic systems including the intestines, the kidneys, the brain, the heart, the circulatory system, urethras, arteries, umbilical lines, and/or the like.

Figure 6:
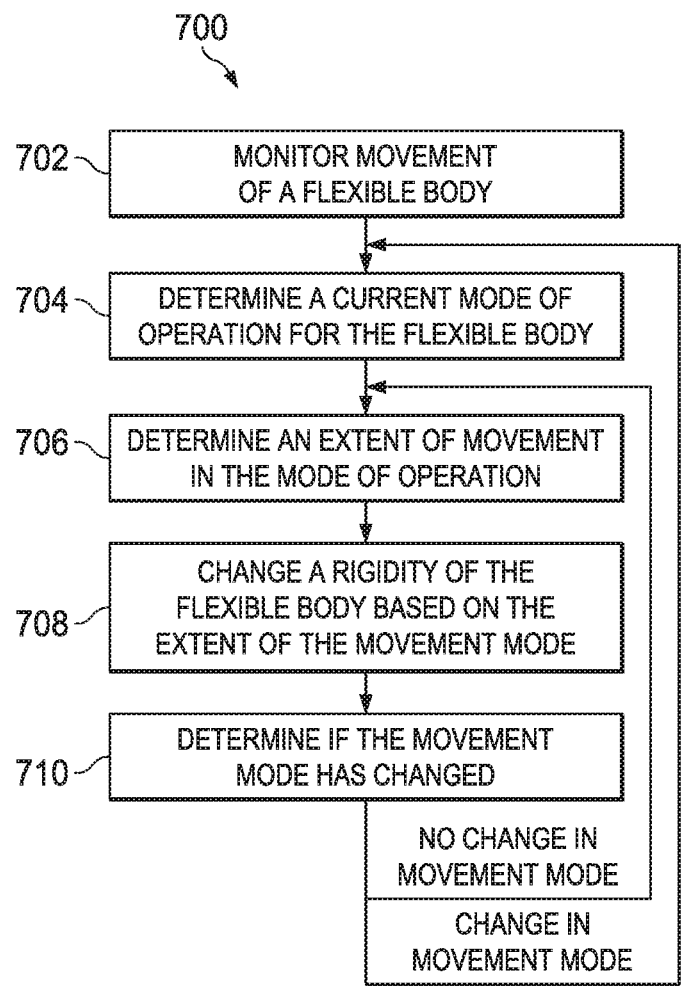
FIG. 6 is a flowchart illustrating an exemplary method for controlling a flexible body.

FIG. 6 is a flowchart illustrating an exemplary method 700 for controlling a flexible body, such as flexible body 216 and/or flexible elongate instrument 510. The method 700 is illustrated in FIG. 6 as a set of operations or processes 702-710. Not all of the illustrated processes 702-710 may be performed in all embodiments of method 700. Additionally, one or more processes that are not expressly illustrated in FIG. 6 may be included before, after, in between, or as part of the processes 702-710. In some embodiments, one or more of the processes 702-710 may be implemented, at least in part, in the form of executable code stored on non-transitory, tangible, computer readable media that when run by one or more processors (e.g., the processors of control system 112) may cause the one or more processors to perform one or more of the processes 702-710. In some examples, the method may begin when the flexible body is initiated into a passageway. In some examples, anatomic passageways may include the intestines, the kidneys, the brain, the heart, the circulatory system, lungs, urethras, arteries, umbilical lines, and/or the like.

During a process 702, movement of the flexible body is monitored. Movement of the flexible body may be measured by a sensor system, such as sensor system 108. One or more sensors, such as position sensor system 220, shape sensor 222, or position measuring device 520 may be used to determine a position of the flexible body. The position may correspond to an insertion depth, such as the position of instrument body 512 along axis A. The monitoring may occur continuously, periodically, and/or at set markers. In some examples, process 702 may be performed concurrently with other steps in method 700. Alternatively, movement can be determined based on commanded motion from an input device such as those described with reference to master assembly 106. In some examples, detection of an input device which would correlate with insertion or retraction can be used to determine movement. In further examples, a user can provide an input by depressing a button or clicking on a button on a touchscreen to indicate an intended change in direction.

Monitoring the movement of the flexible body may include recording state properties of the flexible body such as a current position, a current time, and/or a current control configuration (e.g., current rigidity caused by closed-loop steering wire control) for the flexible body. Alternatively, monitoring the movement of the flexible body may include recording an input magnitude of the input device determined by a measure of size, speed, or velocity of the operator input at the control device, time an input device has been actuated in one direction, pressure placed on an input device, loss of contact between an operators hand and the input device, and/or the like. Recording the current position may include measuring an insertion depth, such as the position of instrument body 512 along axis A. Recording the current rigidity may include measuring one or more forces applied by one or more actuators to one or more wires, such as any of wires 240-242, wires 310-340, and/or wire 430, used to control the steering of the distal end, such as distal end 218, of the flexible body. The rigidity may correspond to an aggregation of the individual forces on each wire, e.g., by average, weighted sum, and/or the like. Measuring the rigidity may also include taking into account external forces applied to flexible body, which may be measured by one or more force and/or pressure sensors, such as one or more strain gauges. In some examples, measuring the rigidity may also include taking into account a measured shape of the distal end, a moment of inertia, Young's modulus, the length of the bending portion of the distal end, and/or the like and/or any combination of these approaches. Measuring the rigidity may include measuring a motor current or an applied actuator torque, such as the torque applied by the actuator to drive shaft 420, used to control the force applied to the one or more wires. In some examples, a rigidity profile of a previous mode may be used to determine the current rigidity based on monitored movement during process 702.

During a process 704, a mode of operation for the flexible body is determined. The mode may correspond to one of retraction, insertion, and parking modes. The mode may be determined based on the movement monitored during process 702. In some examples, the mode determination may be based on elapsed time, velocity, distance traveled of the flexible body, and/or the like and/or any combination thereof. Distance traveled may be equal to the displacement between a current position and the insertion depth recorded during process 702. The current position may correspond to an insertion depth of the flexible body. The elapsed time may be equal to the difference between a current time and the time recorded during process 702. The velocity may be calculated by a sensor, using numerical differentiation, dividing a distance traveled by an elapsed time, and/or by exponential smoothing of velocity sample values, low pass filtering, and/or any combination of these approaches. Numerical differentiation may include backward difference approximation and/or the like. In some examples, the mode determination may be based on input magnitude of the input device determined by a measure of size, speed, or velocity of the operator input at the control device, time an input device has been actuated in one direction, pressure placed on an input device, loss of contact between an operators hand and the input device, and/or the like.

The movement mode may be determined to be the insertion mode when the velocity of the flexible body exceeds a threshold value in an insertion direction or an input device is actuated at a velocity in an insertion direction over a threshold value. Additionally or alternatively, the mode may be determined to be the insertion mode when the velocity of the flexible body or the velocity at which an input device is actuated exceeds a threshold value in the insertion direction for a threshold time. In some examples, the threshold time is between 1 and 10 seconds. In some examples, the threshold velocity is between 0.1-5 millimeters per second in the insertion direction. In some examples, the flexible body is considered to be in the insertion mode until the velocity of the flexible body in the retraction direction exceeds a threshold value. In some examples, the actuation of the input device is considered to be in the insertion mode until the velocity of the actuation of the input device in the retraction direction exceeds a threshold value.

The mode may be determined to be the retraction mode when the velocity of the flexible body exceeds a threshold value in a retraction direction or an input device is actuated at a velocity in a retraction direction over a threshold value. Additionally or alternatively, the mode may be determined to be the retraction mode when the velocity of the flexible body or the velocity at which an input device is actuated exceeds a threshold value in a retraction direction for a threshold time. In some examples, the threshold time is between 1 and 10 seconds. In some examples, the threshold velocity is between 0.1-5 millimeters per second in a retraction direction. In some examples, the flexible body is considered to be in the retraction mode until the velocity of the flexible body in the insertion direction exceeds a threshold value. In some examples, the actuation of the input device is considered to be in the insertion mode until the velocity of the actuation of the input device in the retraction direction exceeds a threshold value. In some examples, the mode may be determined to be the retraction mode when the retracted distance traveled since the last forward motion exceeds a threshold value such as 5 or 10 mm. In some examples, the mode may be determined to be in the retraction mode when the flexible body is commanded via the user input to retract a distance since the last forward motion that exceeds a threshold value such as 5 or 10 mm.

The mode may be determined to be the parking mode when the magnitude of the velocity of the flexible body falls below a threshold value or when the input device is actuated at a velocity that falls below a threshold value. Additionally or alternatively, the mode may be determined to be the parking mode when the velocity of the flexible body or the velocity at which the input device is actuated falls below a threshold value for a threshold time. In some examples, the threshold time is between 1 and 10 seconds. In some examples, the magnitude of the threshold velocity is between 0.1-5 millimeters per second. In some examples, the conditions associated with a threshold velocity and/or a threshold time before determining a change in the mode may be to account for perturbations, sensed noise, cyclic anatomic motion (e.g., respiration and cardiac motion), movement within an anatomy, and/or other movement caused by environmental displacement and/or combinations thereof. In some examples, the mode may be determined to be the parking mode due to loss of operator contact with the input device.

During a process 706, an extent of movement (including lack of movement) in the mode of operation is determined. Using commanded motion from an input device or sensors similar to ones discussed with respect to process 702, the extent of the retraction movement, insertion movement, or parking/stability is measured. The extent of the movement may include measurement of an elapsed time, distance traveled, and/or the like and/or any combination thereof. The distance traveled may be equal to the displacement between a current insertion depth of the flexible body and the insertion depth recorded during process 702 or a displacement in a current input device position and a previous input device position. The elapsed time may be equal to the difference between a current time and the time recorded during process 702.

During a process 708, the rigidity of the flexible body is adjusted based on the extent of the movement. The rigidity may be adjusted by controlling the forces applied by one or more actuators on one more wires used to control the steering of the distal end of the flexible body. Each wire may have the force adjusted by its own force profile that is substantially similar to the rigidity profile. The rigidity may be modified by adjusting a force and/or a torque applied by the one or more actuators to control the pushing and/or pulling of one or more of the one or more wires in the flexible body. In some examples, an actual force or torque applied by an actuator is adjusted. In some examples, a maximum force and/or torque limit is placed on a controller controlling each of the one or more actuators.

During the retraction mode, the rigidity of the flexible body may be decreased according to a rigidity profile, such as rigidity profile 600. $K_1$ may be set to the rigidity recorded during process 702 and decreased until the rigidity is at a final rigidity value such as $k_2$ from rigidity profile 600. The final rigidity may be set at a nominal, possibly non-zero value, to retain at least some control over a bend in the distal end of the flexible body, an instrument deployed at the distal end of the flexible body, and/or the like. During the insertion mode, the rigidity of the flexible body may be increased according to a rigidity profile, such as rigidity profile 650. $K_3$ may be set to the rigidity recorded during process 702 and increased until the rigidity is at a final rigidity such as $k_4$ from rigidity profile 650. During the parking mode, the final rigidity may provide sufficient stiffness to the flexible body to steer the advancing flexible body and control the orientation of a medical tool deployed from the flexible body. Alternatively, during the parking mode, rigidity may be increased in a locked mode so that the flexible body may be properly articulated or may act as an effective stationary platform.

During process 708, the rigidity may be adjusted based upon additional factors such as by one or more external forces applied to the flexible body, a shape of the flexible body, a sensitivity of the anatomy forming the passageways, a curvature of the anatomy, one or more operator preferences, and/or the like and/or any combination of these approaches.

During a process 710, it is determined whether a change in movement mode occurs. For example, a change from insertion mode to retraction or park mode may be determined or a change from retraction mode to insertion or park mode may be determined. The change in mode may be determined based on an elapsed time, velocity, distance traveled and/or the like and/or any combination thereof. In some examples, a change in mode is determined based on a change in direction of movement of flexible body. In some examples, a change in mode is determined when the velocity of the flexible body exceeds a threshold value in a direction opposite of the previously determined movement mode. The conditions associated with a threshold velocity and/or a threshold time before determining a change in the mode may be needed to account for perturbations, sensed noise, cyclic anatomic motion (e.g., respiration and cardiac motion), movement within an anatomy, and/or other movement caused by environmental displacement and/or combinations thereof. In some embodiments, the parking mode is optional with the mode of operation being limited to the retraction mode and insertion mode.

If there is a change in mode determined at process 710, the method may be repeated starting at process 704. If there is no change in mode, the method may be repeated starting at process 706.

As discussed above and further emphasized here, FIG. 6 is one example which should not unduly limit the scope of the claims. One of ordinary skill in the art would recognize many variations, alternatives, and modifications. In some embodiments, during a transition from a first mode to a second mode, the rigidity profile of the first mode may continue as if no change in mode occurred. In some examples, during a transition from the insertion mode to the parking mode, the rigidity may continue to be increased according to the rigidity profile of the insertion mode as if insertion is continuing without interruption. In some examples, during a transition from the parking mode to the insertion mode, the rigidity may continue to be increased according to the rigidity profile of the parking mode as if parking is continuing without interruption. In some examples, during a transition from the retraction mode to the parking mode, the rigidity may continue to be decreased according to the rigidity profile of the retraction mode as if retraction is continuing without interruption. In some examples, during a transition from the parking mode to the retraction mode, the rigidity may continue to be decreased according to the rigidity profile of the parking mode as if parking is continuing without interruption.

In some embodiments, one or more of the processes 702-710 of method 700 may be implemented, at least in part, in the form of executable code stored on non-transient, tangible, machine-readable media that when run by one or more processors (e.g., control system 112) may cause the one or more processors to perform one or more of the processes 702-710. Additionally, one or more elements in embodiments and examples may be implemented in software to execute on the one or more processors. When implemented in software, the elements of the embodiments are essentially the code segments to perform the necessary tasks. The program or code segments can be stored in a non-transitory, processor-readable storage medium or device, including any medium that can store information including an optical medium, semiconductor medium, and magnetic medium. Non-transitory, processor-readable storage device examples include an electronic circuit, a semiconductor device, a semiconductor memory device, a read only memory (ROM), a flash memory, an erasable programmable read only memory (EPROM), a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by control system 112 or one or more processors thereof.

Figure 7:
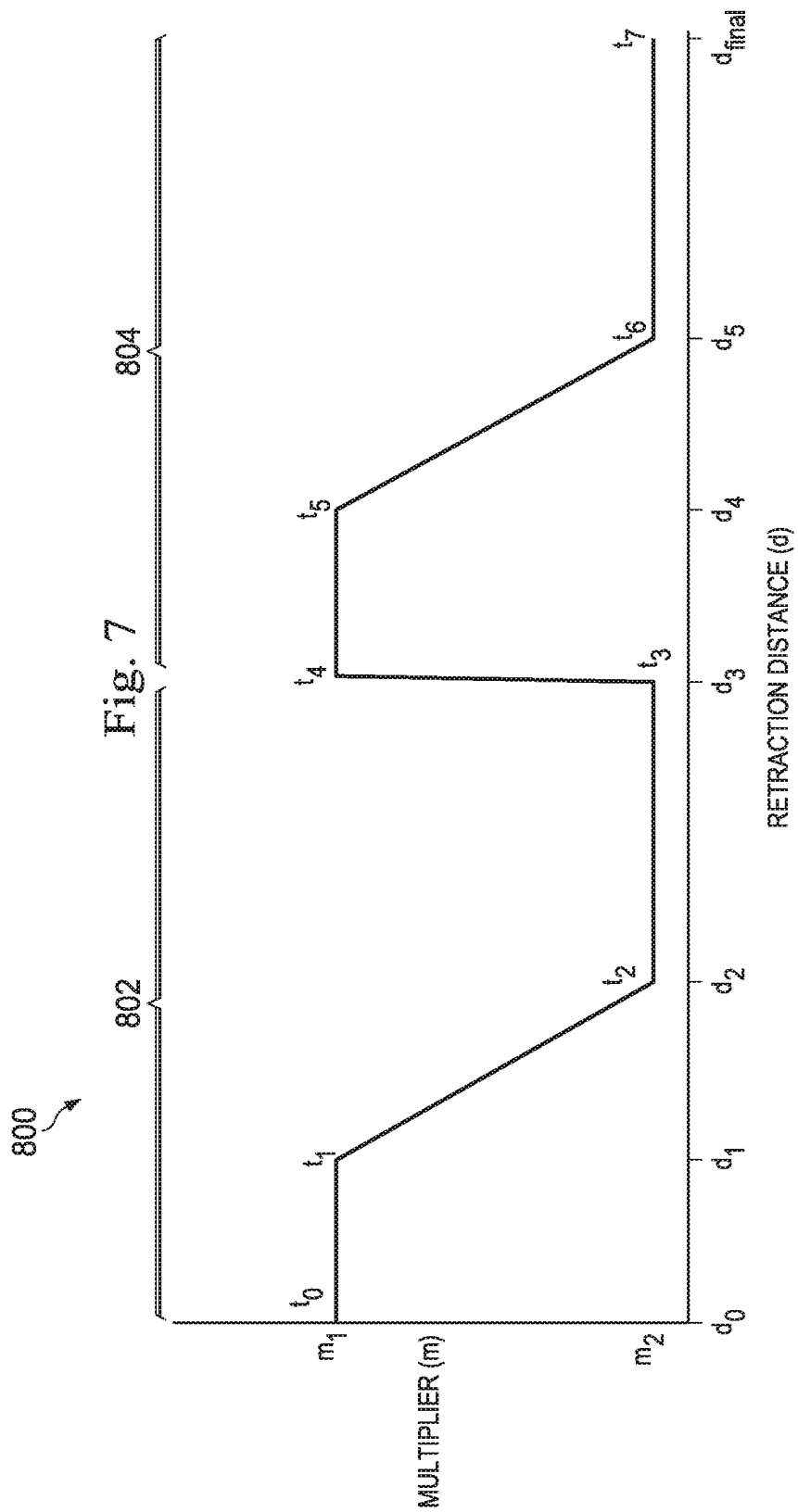
FIG. 7 illustrates a rigidity multiplier profile applied during an exemplary application of the method of FIG. 6 shown in relation to a retraction distance.

The previously described rigidity profile 600 and/or 650 may implement a scaling factor and/or torque multiplier used to scale a force and/or torque that is applied by the one or more actuators. FIG. 7 illustrates a rigidity multiplier profile 800 applied during an exemplary application of method of retraction over a retraction distance 802 and over a retraction distance 804. In some examples, a multiplier m may be representative of a scaling factor and/or torque multiplier used to scale a force and/or torque applied by the one or more actuators during processes 708 to adjust the rigidity of the flexible elongate instrument. Rigidity multiplier profile 800 is a graphical representation of a possible variation of the multiplier m, illustrated by curve 810 according to retraction distance, designated by d. Times $t_0$-$t_7$ show the relationships between retraction distances $d_0$-$d_{final}$ and multiplier m over time. In some examples, the multiplier m may range from a value $m_1$ of 1.0 or near 1.0 at which the flexible instrument is relatively rigid to a value $m_2$ of zero or near zero at which the flexible instrument is relatively slack. In some examples, the torque is a function of the multiplier and the maximum torque, $\tau_{max}$ that may be applied by the actuator, illustrated by Equation 1. In some examples, the torque determined by Equation 1 may be applied by the respective controllers either as an actual torque to be applied by the respective actuators or as a maximum torque limit to be applied on the respective actuators.

$$\tau = \tau_{max} \times m(d,t) \qquad (1)$$

In some examples, when the forces are being scaled, $\tau$ and $\tau_{max}$ are replaced by f and $f_{max}$, accordingly; with an actual force or maximum force limit being set.

In FIG. 7, at an initial position $d_0$, the flexible instrument has been inserted into an anatomic passageway and placed in a park mode with a multiplier set at $m_1$. In one example, the flexible instrument may be inserted 100 mm into the anatomic passageways when parked. The flexible instrument then enters a retraction mode. In the initial stage of the retraction mode, the flexible instrument moves from the initial position $d_0$ and a retracted distance $d_1$ while the multiplier remains unchanged or approximately unchanged at or near the value $m_1$. In one example, the extent of the flexible instrument retraction between $d_0$ and $d_1$ may be approximately 5 mm. The distance between $d_0$ and $d_1$ may be traversed over a time period between $t_0$ and $t_1$. After the flexible instrument has been retracted a distance $d_1$, the multiplier in begins to reduce. Over a retraction distance between $d_1$ and $d_2$, the multiplier m is reduced from the value $m_1$ (e.g., relatively rigid) to the value $m_2$ (e.g., relatively slack). The distance between $d_1$ and $d_2$ may be traversed over a time period between $t_1$ and $t_2$. In this example, the extent of the flexible instrument retraction may be approximately 10 mm between $d_1$ and $d_2$. As the flexible instrument continues to retract from distance $d_2$ to $d_3$, the multiplier value remains at $m_2$. In one example, the flexible instrument may retract approximately 35 mm between $d_2$ and $d_3$. The distance between $d_2$ and $d_3$ may be traversed over a time period between $t_2$ and $t_3$.

At the distance $d_3$, the flexible instrument exits the retraction mode and enters a park mode. In the park mode, the flexible instrument remains at the distance $d_3$ for a time period between $t_3$ and $t_4$. In this example, while in the park mode, the multiplier value ramps up to $m_1$ (e.g., relatively rigid). This transition from multiplier value $m_2$ to $m_1$ may occur abruptly over a short period of time or may follow a more gradual transition profile based on elapsed time.

At time $t_4$, the flexible instrument exits the park mode and enters the retraction mode again. In the initial stage of the second retraction mode, the flexible instrument moves from the parked distance $d_3$ to a retracted distance $d_4$ while the multiplier remains unchanged or approximately unchanged at or near the value $m_r$. In this example, the flexible instrument may retract approximately 5 mm between $d_3$ and $d_4$. The distance between $d_3$ and $d_4$ may be traversed over a time period between $t_4$ and $t_5$. After the flexible instrument has been retracted a distance $d_4$, the multiplier m begins to reduce. Over a retraction distance between $d_4$ and $d_5$, the multiplier m is again reduced from the value $m_1$ (e.g., relatively rigid) to the value $m_2$ (e.g., relatively slack). The distance between $d_4$ and $d_5$ may be traversed over a time period between $t_5$ and $t_6$. In one example, the flexible instrument may retract approximately 10 mm between $d_4$ and $d_5$. As the flexible instrument continues to retract from distance $d_5$ to $d_{final}$ where the flexible instrument is fully retracted from the patient anatomy, the multiplier value remains at $m_2$. In one example, the flexible instrument may retract approximately 35 mm between $d_2$ and $d_3$. The distance between $d_5$ and $d_{final}$ may be traversed over a time period between $t_6$ and $t_7$.

In a drive movement mode such as insertion or retraction, various sub-modes of the control system may be selected to alter the rigidity of the flexible body based on a sub-mode specific rigidity profile.

Figure 8:
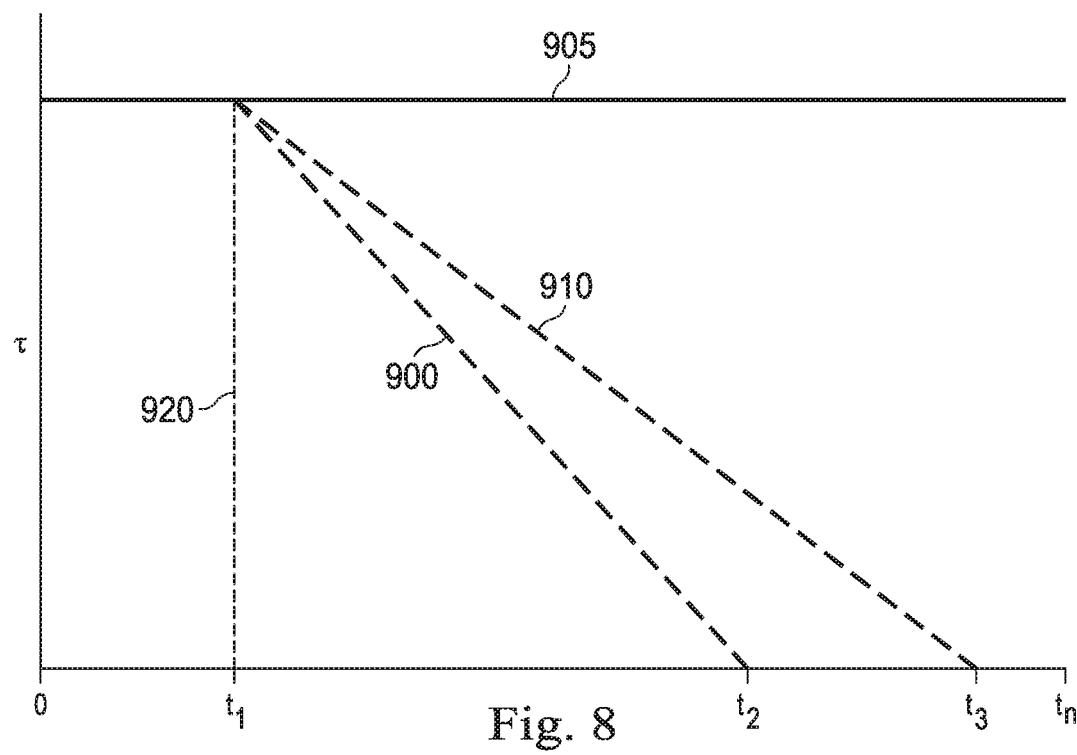

One example of a sub-mode of a drive movement mode is a full passive sub-mode. The full passive sub-mode may be operator-selected using for example, an identifying input to the control device at the master assembly 106 (e.g. a double or multiple tap of a "passive" button located on the control device), a voice command, or an anatomical gesture command. FIG. 8 illustrates a rigidity profile 900 that may be used in the full passive sub-mode. According to the rigidity profile 900, the rigidity of the flexible body is reduced as the actuator torque is reduced from an operating torque 905 to a torque of approximately zero over the time period between the time of the operator input (t=0) and a predetermined time (t=$t_2$). In this embodiment, the rigidity profile 900 is linear but in alternative embodiments, the rigidity profile in full passive sub-mode may be non-linear. The full passive sub-mode may be suitable for use when the procedure is complete, and the operator is retracting the flexible body from the patient anatomy using the master assembly. Alternatively the full passive sub-mode may be suitable when the flexible catheter is positioned within a tight bend in an anatomic passageway, and the operator would like to relieve rigidity in the flexible catheter (and therefore the anatomic passageway) to, for example, allow passage of a biopsy needle. The control system may remain in the full passive sub-mode until the operator selects a different mode or until another predefined condition occurs.

Figure 9:
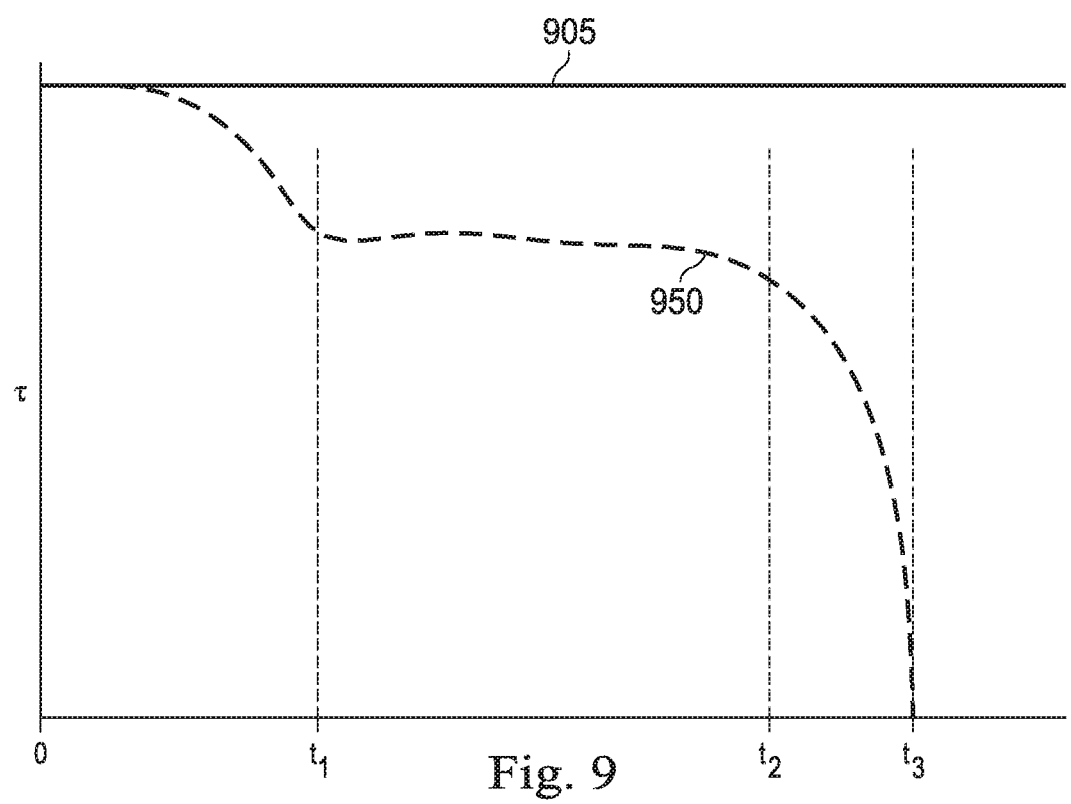

Another example of a sub-mode of a drive movement mode is a slow passive sub-mode. The slow passive sub-mode may be operator-selected using for example, an identifying input to the control device at the master assembly 106 (e.g. holding down the "passive" button located on the control device for the duration of the slow passive sub-mode), a voice command, or an anatomical gesture command. FIG. 8 illustrates a rigidity profile 910 that may be used in the slow passive sub-mode. According to the rigidity profile 910, the rigidity of the flexible body is reduced as the actuator torque is reduced from an operating torque 905 to a torque of approximately zero over the time period between the time of the operator input (t=0) and a predetermined time (t=$t_3$). As compared to the full passive rigidity profile 910, the slow passive rigidity profile reduces torque at a slower rate. In this embodiment, the rigidity profile 910 is linear but in alternative embodiments, the rigidity profile in full passive sub-mode may be non-linear. FIG. 9 illustrates such a non-linear profile 950. According to the rigidity profile 950, the rigidity of the flexible body is reduced as the actuator torque drops quickly between an initial interval ($t_0$-$t_1$). The actuator torque is relatively stable between an interval ($t_1$-$t_2$) and drops quickly to a torque of approximately zero over an interval ($t_2$-$t_3$). The slow passive sub-mode may be suitable for use when the operator makes slight adjustments to the flexible body position in the patient anatomy where the short incremental distances moved by the flexible body are too small to effectively reduce the actuator torque under a normal drive movement mode such as insertion or retraction. At time $t_2$, enough time has elapsed that it may be likely that the operator intends to withdraw the flexible body from the patient anatomy or make significant withdrawal movements. Thus from $t_2$ to $t_3$ the reduction in torque can be rapid. The control system may remain in the slow passive sub-mode until, for example, the operator releases the passive button. When the passive button is released, the control system may return to the previous mode of operation by ramping up torque to a previous torque level or to the operating torque level using a linear or non-linear ramp up profile.

Another example of a sub-mode of a drive movement mode is an insertion clutch sub-mode. The insertion clutch sub-mode may be operator-selected using for example, an identifying input to a clutch input located on a carriage of the manipulator assembly 102 (e.g. the operator may depress and hold down a clutch input button or may double or multiple tap the clutch input button) or on another component of the system 100. Alternatively another type of user input including a voice command or an anatomical gesture command. FIG. 8 illustrates a rigidity profile 920 that may be used in the insertion clutch sub-mode. According to the rigidity profile 920, the rigidity of the flexible body is reduced immediately as the actuator torque is reduced from an operating torque to a torque of approximately zero over an instantaneous or relatively short time period at the time of the operator input (t=$t_1$). In this embodiment, the rigidity profile 920 is linear but in alternative embodiments, the rigidity profile in insertion clutch sub-mode may be non-linear over a relatively short time period. In this sub-mode, the master assembly 106 may not accept user commands to control the manipulator or an attached instrument, and the actuators that provide motion along an insertion path may be disabled. The insertion clutch sub-mode may be suitable for use when the operator wants to quickly remove the flexible body from the patient anatomy in an emergency situation or for another clinical purpose. In the insertion clutch sub-mode, the operator may manually retract the flexible body by moving an insertion stage of the manipulator assembly 102 to which the instrument 104 is coupled. The control system may remain in the insertion clutch sub-mode until the operator releases the clutch input button or another release condition is met.

Another example of a sub-mode of a drive movement mode is an auto-passive sub-mode. The auto-passive passive sub-mode may be operator-selected using for example, an identifying input to the control device at the master assembly 106 (e.g. a single tap of a "passive" button located on the control device), a voice command, or an anatomical gesture command. FIG. 10 illustrates a rigidity profile 960 that may be used in the auto-passive sub-mode. According to the rigidity profile 960, the rigidity of the flexible body is reduced as the actuator torque is reduced from an operating torque 905 to a torque of approximately zero based on an input magnitude. The input magnitude may be a measure of size or speed of the operator input at the control device of the master assembly 106 correlating to a measure of desired distance the flexible body is commanded to be moved. For example, if the control device is a scroll wheel on the master assembly 106, small retractions on the scroll wheel are considered a small input magnitude in the auto-passive sub-mode correlating with a short commanded movement distance, and large retractions on the scroll wheel are considered a large input magnitude in the auto-passive sub-mode correlating with a large commanded movement distance. With the rigidity profile 960, small input magnitudes cause the flexible body to remain under active control, at the operating torque 905. This allows an operator to perform fine adjustments in position without losing the orientation of the distal end of the flexible body. With the rigidity profile 960, large input magnitudes cause the actuator torque to become reduced from an operating torque to a torque of approximately zero. This allows the operator to move the flexible body large distances or remove the flexible body from the patient anatomy with little or no rigidity. In this embodiment, the rigidity profile 960 is linear but in alternative embodiments, the rigidity profile in auto-passive sub-mode may be non-linear. The control system may remain in the auto-passive sub-mode during a particular movement mode (e.g. retraction), but when the operator changes movement modes (e.g., returns to active insertion), the control system switches out of the auto-passive sub-mode and the actuator torque returns to the operating torque 905 gradually or according to a configurable linear or non-linear transition profile. Alternatively, exiting the auto-passive sub-mode may be accomplished by another type of user input such as a switch.

Note that the processes and displays presented may not inherently be related to any particular computer or other apparatus. The required structure for a variety of these systems will appear as elements in the claims. In addition, the embodiments are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A computer-assisted medical system comprising:
   a flexible elongate instrument comprising a plurality of wires extending from a proximal end of the flexible elongate instrument to a distal end of the flexible elongate instrument, each wire of the plurality of wires useable to steer the distal end; and
   a control system coupled to the flexible elongate instrument and configured to:
      monitor movement of the flexible elongate instrument along a longitudinal central axis;
      determine an extent of motion of the flexible elongate instrument in a first direction along the longitudinal central axis based on the monitoring; and
      alter a rigidity of the flexible elongate instrument based on a rigidity profile relative to the extent of motion by adjusting one or more forces applied by the plurality of wires to the distal end of the flexible elongate instrument.

2. The computer-assisted medical system of claim 1, wherein the control system is further configured to determine the extent of motion based on an elapsed retraction time.

3. The computer-assisted medical system of claim 1, wherein the control system is further configured to determine the extent of motion based on a difference between a current insertion depth and an insertion depth recorded at a start of motion.

4. The computer-assisted medical system of claim 1, wherein the control system is further configured to determine a change in a mode of operation when a velocity of the flexible elongate instrument exceeds a threshold value in a second direction, opposite the first direction, the velocity of the flexible elongate instrument corresponding to a change in depth of the flexible elongate instrument in a patient anatomy.

5. The computer-assisted medical system of claim 4, wherein the control system is further configured to determine the change in the mode of operation when the velocity of the flexible elongate instrument exceeds the threshold value in the second direction for a threshold time.

6. The computer-assisted medical system of claim 4, wherein the control system is further configured to, in response to determining that the mode of operation is changed, determine a second extent of motion in the second direction based on the monitoring.

7. The computer-assisted medical system of claim 6, wherein the control system is further configured to determine the second extent of motion in the second direction based on an elapsed insertion time.

8. The computer-assisted medical system of claim 6, wherein the control system is further configured to determine the second extent of motion in the second direction based on a difference between a current instrument depth and a depth recorded at a start of motion in the second direction.

9. The computer-assisted medical system of claim 6, wherein the control system is further configured to determine the second extent of motion in the second direction based on a combination of an elapsed insertion time and a difference between a current instrument depth and a depth recorded at a start of motion in the second direction.

10. The computer-assisted medical system of claim 1, wherein the control system is further configured to determine a change in a mode of operation to a parking mode when a magnitude of a velocity of the flexible elongate instrument falls below a threshold value.

11. The computer-assisted medical system of claim 10, wherein the control system is further configured to determine the change in the mode of operation to the parking mode when the magnitude of the velocity of the flexible elongate instrument falls below the threshold value for a threshold time.

12. The computer-assisted medical system of claim 10, wherein the control system is further configured to, in response to determining that the mode of operation is changed to the parking mode, determine an extent of a parking of the flexible elongate instrument based on the monitoring.

13. The computer-assisted medical system of claim 12, wherein the control system is further configured to, in response to determining that the mode of operation is changed to the parking mode, increase the rigidity of the flexible elongate instrument based on the extent of the parking by adjusting the one or more forces applied by the plurality of wires to the distal end of the flexible elongate instrument.

14. The computer-assisted medical system of claim 12, wherein the control system is further configured to, in response to determining that the mode of operation is changed to the parking mode, decrease the rigidity of the flexible elongate instrument based on the extent of the parking according to a previous rigidity profile applied during motion of the flexible elongate instrument.

15. The computer-assisted medical system of claim 12, wherein the control system is further configured to, in response to determining that the mode of operation is changed to the parking mode, maintain a current rigidity of the flexible elongate instrument.

16. The computer-assisted medical system of claim 12, wherein the control system is further configured to determine the extent of the parking based on an elapsed parking time.

17. A method of controlling a medical device, comprising:
   monitoring commanded movement of a flexible elongate instrument, wherein the flexible elongate instrument comprises a plurality of wires extending from a proximal end of the flexible elongate instrument to a distal end of the flexible elongate instrument, each of the plurality of wires useable to steer the distal end of the flexible elongate instrument; and determining an extent of a commanded motion of the flexible elongate instrument based on the monitoring; and altering a rigidity of the flexible elongate instrument based on a rigidity profile relative to the extent of the commanded motion by adjusting one or more forces applied by one or more wires of the plurality of wires to the distal end of the flexible elongate instrument.

18. The method of claim 17, wherein the determining the extent of the commanded motion is based on an elapsed retraction time.

19. A non-transitory machine-readable medium comprising a plurality of machine-readable instructions which, when executed by one or more processors associated with a flexible elongate instrument, are adapted to cause the one or more processors to perform a method comprising:

monitoring movement of the flexible elongate instrument, the flexible elongate instrument comprising a plurality of wires extending from a proximal end of the flexible elongate instrument to a distal end of the flexible elongate instrument, each of the plurality of wires useable to steer the distal end of the flexible elongate instrument;

determining an extent of a motion of the flexible elongate instrument in a first direction based on the monitoring; and altering a rigidity of the flexible elongate instrument based on a rigidity profile relative to the extent of the motion by adjusting one or more forces applied by one or more wires of the plurality of wires to the distal end of the flexible elongate instrument.

20. The non-transitory machine-readable medium of claim 19, wherein the plurality of machine-readable instructions are adapted to cause the one or more processors to perform the method that further includes determining a change in a mode of operation when a velocity of the flexible elongate instrument exceeds a threshold value in a second direction, opposite the first direction, the velocity of the flexible elongate instrument corresponding to a change in depth of the flexible elongate instrument in a patient anatomy.

* * * * *